(12) United States Patent
Jones et al.

(10) Patent No.: US 6,585,662 B1
(45) Date of Patent: Jul. 1, 2003

(54) PNEUMOTACHOMETER

(75) Inventors: Terrence K. Jones, Sharon, MA (US); Donald J. Brooks, Melrose, MA (US)

(73) Assignee: Boston Medical Technologies, Inc., Wakefield, MA (US)

( * ) Notice: Subject to any disclaimer, the term of this patent is extended or adjusted under 35 U.S.C. 154(b) by 274 days.

(21) Appl. No.: 09/767,817

(22) Filed: Jan. 19, 2001

(51) Int. Cl.[7] ................................................ A61B 5/08
(52) U.S. Cl. ...................... 600/538; 600/532; 600/529; 73/861.52
(58) Field of Search ................................ 600/538, 532, 600/529, 543, 533, 484; 73/861.52, 861.61

(56) References Cited

U.S. PATENT DOCUMENTS

| | | | |
|---|---|---|---|
| 4,905,709 A | 3/1990 | Bieganski et al. | |
| 5,038,773 A | 8/1991 | Norlien et al. | |
| 5,134,890 A | 8/1992 | Abrams | 73/861.52 |
| 5,360,009 A | 11/1994 | Herskovitz | |
| 5,735,287 A | 4/1998 | Thomson | |
| 5,800,361 A * | 9/1998 | Rayburn | 600/532 |
| 6,090,049 A | 7/2000 | Cha | 600/538 |
| 6,099,481 A * | 8/2000 | Daniels et al. | 600/538 |
| 6,142,952 A | 11/2000 | Behbehani et al. | 600/533 |
| 6,179,784 B1 * | 1/2001 | Daniels et al. | 600/538 |
| 6,183,423 B1 * | 2/2001 | Gaumond et al. | 600/529 |
| 6,251,082 B1 * | 6/2001 | Rayburn | 600/532 |
| 6,379,311 B1 * | 4/2002 | Gaumond et al. | 600/529 |

OTHER PUBLICATIONS

"Filtrete™ Air Filter Media Type G, GS and GSB" (Technical Data of 3M Filtration Products of St. Paul, MN), 4 pgs.
International Search Report for PCT/US01/46787.

* cited by examiner

*Primary Examiner*—Teresa Walberg
*Assistant Examiner*—Fadi H. Dahbour
(74) *Attorney, Agent, or Firm*—Daly, Crowley & Mofford, LLP

(57) ABSTRACT

A disposable differential pressure pneumotachometer includes an inlet chamber having an air inlet, an outlet chamber having an air outlet, and a resistive element disposed between the inlet and outlet chambers. Air flow across the resistive element results in a pressure gradient which is measured to provide air flow rate. According to one aspect of the invention, the pressure port through which the static pressure in the inlet chamber is sensed is disposed in the outlet chamber. According to a further aspect of the invention, the resistive element comprises a bacterial filter material. Also described is a pneumotachometer in which at least one pressure port is covered with a bacterial filter material.

20 Claims, 8 Drawing Sheets

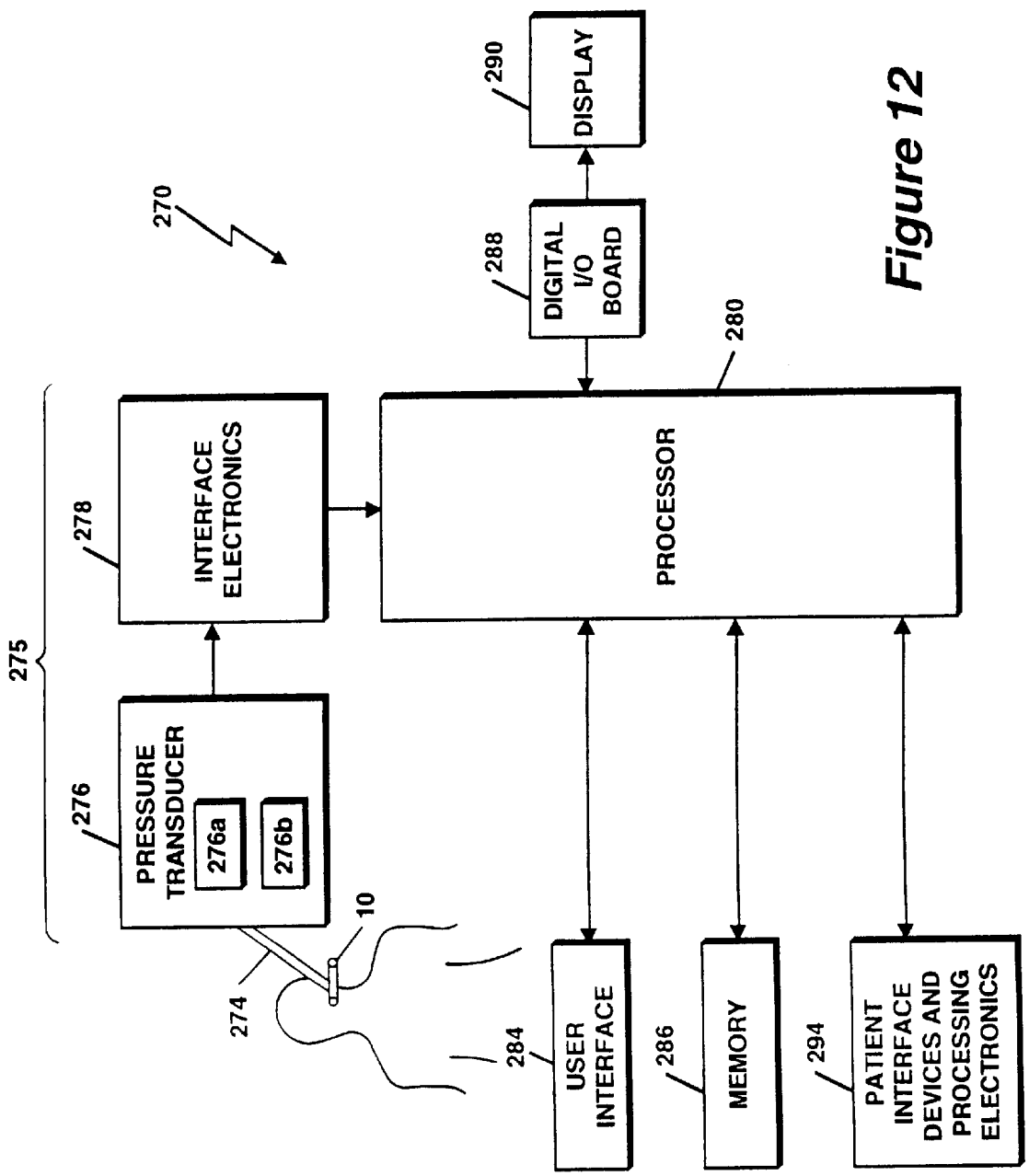

PNEUMOTACHOMETER

STATEMENTS REGARDING FEDERALLY SPONSORED RESEARCH

Not applicable.

CROSS-REFERENCE TO RELATED APPLICATIONS

Not applicable.

BACKGROUND OF THE INVENTION

Pneumotachometers, or flow sensors, are used to measure inhalation and exhalation flow rates. A spirometer is a medical device which uses flow rate signals from a pneumotachometer to measure the volume of air entering and leaving the lungs and conduct specific pulmonary function assessments.

One type of pneumotachometer is a differential pressure pneumotachometer in which an air-resistive element located in the air flow path creates a pressure drop which is proportional to the air flow rate. A pressure transducer converts the differential pressure across the resistive element into an electrical signal indicative of air flow rate. The flow rate signal can be integrated to provide an indication of breath or "flow" volume.

Respiratory flow rates and breath volumes are measured for use in various medical diagnostic tests. For example, heart rate variability analysis, which is used to evaluate a patient's autonomic nervous system function, utilizes respiratory flow rate measurement. In heart rate variability analysis, the patient's autonomic nervous system is exercised by performing various breathing maneuvers, or tests. Two such tests are the Valsalva test and the metronomic deep breathing test. The Valsalva test requires that the patient forcibly exhale at a predetermined pressure, such as 40 mmHg, for a predetermined duration, such as 15 seconds, during which the heart rate is monitored. Thereafter, the patient rests for a predetermined duration. The result of the Valsalva test is a ratio of the highest heart rate (as indicated by the shortest R-R interval in the patient's ECG signal) during the breathing maneuver to the lowest heart rate (as indicated by the longest R-R interval) during a rest period after the maneuver. In accordance with the metronomic deep breathing test, which is sometimes referred to as the E/I test, the patient is instructed to breathe deeply at a frequency of 6 cycles/minute, which has been shown to produce predictable heart rate variability in healthy individuals. The result of the metronomic deep breathing test is a ratio of the average of the heart rate peaks from the ECG signal to the average of the heart rate troughs. Measurement of the patient's breath flow rate during these breathing maneuvers is used to monitor compliance with the desired breathing maneuver and thus, to ensure accurate testing.

Various differential pressure pneumotachometers are available. One such device is a disposable pneumotach from Advanced Biosensor of Columbia, S.C. This device has an inlet into which a patient breathes, an outlet through which air exits or enters the device depending on whether the patient is exhaling or inhaling, respectively, and a thin membrane positioned between the inlet and the outlet, so as to divide the device into an inlet chamber and an outlet chamber. The membrane is comprised of a fiber mesh, such as a nylon mesh, which restricts the air flow enough to cause a pressure drop from one side of the membrane to the other. A first port for sensing the inlet chamber pressure is located in the inlet chamber and a second port for sensing the outlet chamber pressure is located in the outlet chamber. Each pressure port is adapted for coupling to an input of a differential pressure transducer through a respective tube. In some testing applications, such as the Valsalva test, a plug is placed on the outlet in order to permit a predetermined air pressure to be achieved by further restricting air flow. The pneumotachometer is disposable, but the tubes coupled between the pneumotachometer and the pressure transducer as well as the Valsalva plug are reusable.

One problem with such a pneumotachometer is possible contamination. As the patient breathes into the pneumotachometer, contagions can enter the reusable tubes through the pressure sensing ports and can also contaminate the reusable Valsalva plug, thereby potentially causing cross-contamination between patients. Further, condensation entering the tubes can deteriorate the performance of the pressure transducer and other processing electronics.

A disposable bacterial filter device, such as the VIRO III disposable filter of A-M System, Inc. of Carlsborg, Wash., is sometimes used in conjunction with a pneumotachometer in order to reduce contamination. The disposable filter device includes a bacterial filter material which acts as a barrier to bacteria and viruses. However, use of a bacterial filter device in conjunction with a pneumotachometer increases the cost and decreases the ease of use of the device.

SUMMARY OF THE INVENTION

According to the invention, a pneumotachometer includes an inlet, an outlet, a resistive element positioned between the inlet and outlet to divide the device into an inlet chamber and an outlet chamber, and a pressure port disposed in the outlet chamber through which the static pressure in the inlet chamber is sensed. Since the pressure port for sampling the inlet chamber pressure is located in the outlet chamber and is isolated from the inlet chamber by the resistive element, the resistive element serves to isolate the pressure port, and also the reusable tubing coupled to the pressure port, from contagions. With this arrangement, the likelihood of that contagions introduced into the device through the inlet will contaminate apparatus coupled to the pressure port is reduced.

In one embodiment, a pressure sampling channel has a first portion disposed in the inlet chamber in gaseous communication with the inlet chamber through at least one aperture and a second portion disposed in the outlet chamber in gaseous communication with the first channel portion and with the pressure port. The first and second portions of the pressure sampling channel are divided by a portion of the resistive element. Because there is negligible air flow through the pressure sampling channel, there is negligible pressure gradient across the portion of the resistive element located in this region. As a result, the pressure sampled via the pressure port provides an accurate indication of the static pressure in the inlet chamber.

In one embodiment, the aperture in the inlet portion of the sampling channel is provided in the form of slots. With this arrangement, manufacture of the pneumotachometer by injection molding is facilitated.

According to a further aspect of the invention, a pneumotachometer having an inlet and an outlet and a resistive element positioned between the inlet and outlet to divide the device into an inlet chamber and an outlet chamber is provided with a resistive element in the form of a bacterial filter material. The bacterial filter material comprises a web of electrostatically charged, hydrophobic fibers. Use of a bacterial filter material for the resistive element improves the isolation between the patient's mouth and a pressure port located in the outlet chamber. The bacterial filter material additionally serves as a barrier between the patient's mouth and the Valsalva plug covering the outlet during the Valsalva maneuver.

According to a further aspect of the invention, one or more pressure ports of the pneumotachometer is covered by a bacterial filter material. This arrangement further reduces contamination of apparatus coupled to the covered pressure port.

The pressure in the outlet chamber may be sensed through a second pressure port or may be presumed to be at ambient. In one embodiment, the second pressure port is disposed in a wall of the outlet chamber and may or may not be protected by a bacterial filter. In an alternative embodiment, the second pressure port is disposed in a wall of the inlet chamber and is in isolated gaseous communication with the outlet chamber through a pressure sampling channel or tube.

BRIEF DESCRIPTION OF THE DRAWINGS

The foregoing features of this invention, as well as the invention itself, may be more fully understood from the following description of the drawings in which:

FIG. 12 is a block diagram of a medical testing system including a spirometer utilizing a pneumotachometer of the present invention.

DESCRIPTION OF THE PREFERRED EMBODIMENT

Figure 1:
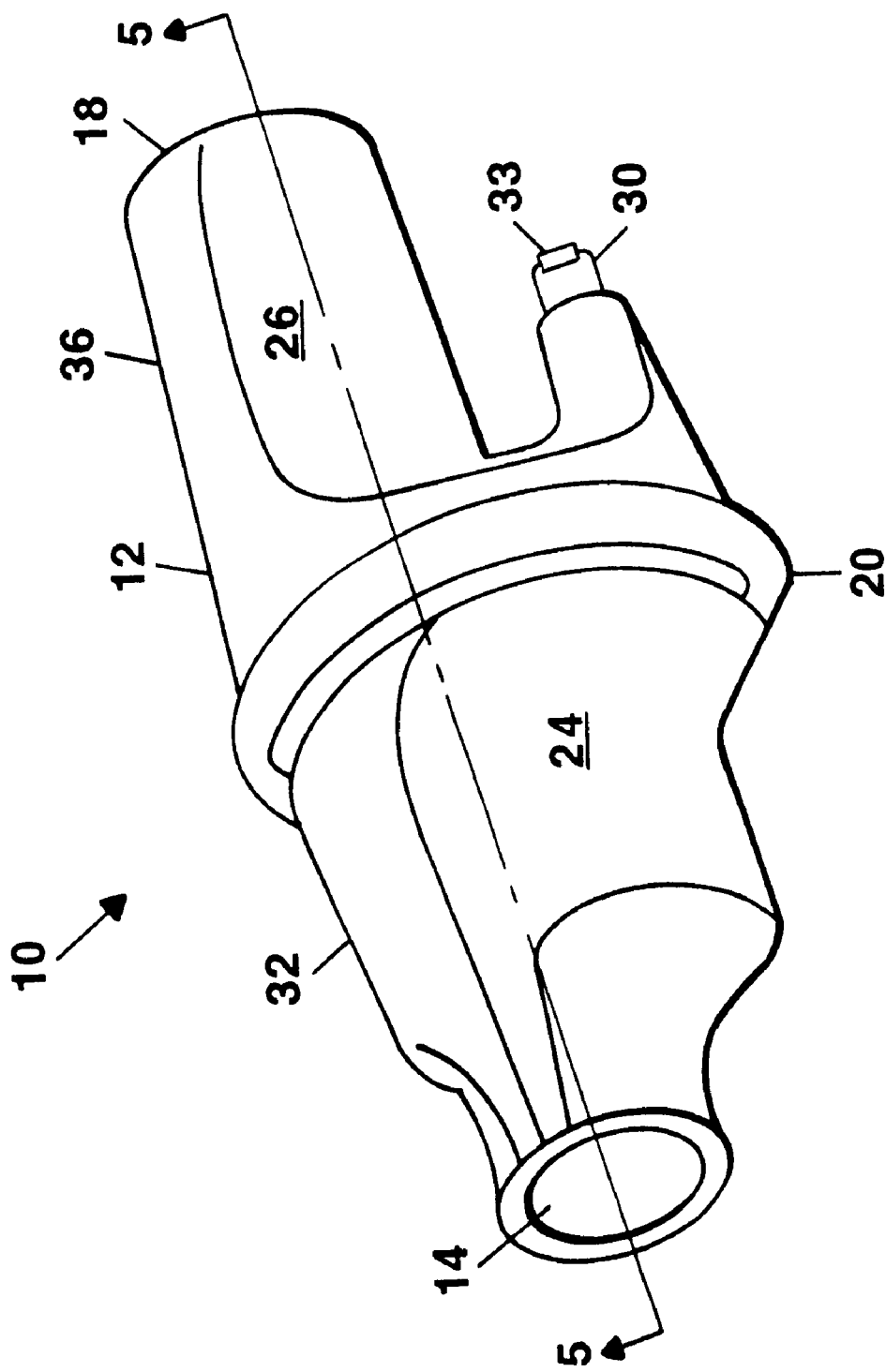
FIG. 1 is an isometric view of a pneumotachometer according to the invention.

Referring to FIG. 1, a pneumotachometer 10 includes a housing 12 having an inlet 14 through which a patient breathes and an outlet 18 through which air exits or enters the pneumotachometer depending on whether the patient is exhaling or inhaling, respectively. A resistive element 20 divides the housing 12 into an inlet chamber 24 and an outlet chamber 26 and causes a pressure differential to be developed between the chambers as air flows between the inlet and outlet chambers.

According to one aspect of the invention, a pressure port 30 for sensing the static pressure in the inlet chamber 24 is located in the outlet chamber 26, as shown. With this arrangement, the resistive element 20, in addition to creating a pressure differential between the inlet and outlet chambers, serves the additional purpose of isolating the pressure port 30 from contagions from the patient's mouth. This is because the resistive element 20 is located between the inlet chamber 24 and the pressure port 30.

In use, the pneumotachometer 10 is adapted for coupling to electronics 275 (FIG. 12) in order to measure aspects of the patient's respiration for use in various medical testing applications, such as the illustrative heart rate variability monitor of FIG. 12. More particularly, the pressure port 30 is adapted for coupling to a pressure transducer 276 through a tube 274 (FIG. 12). For this purpose, the port 30 is provided with a Luer lock fitting 33 for coupling to a Luer lock of the tube 274. It will be appreciated by those of ordinary skill in the art however that other tube fittings may alternatively be used.

The pressure gradient across the resistive element 20 (i.e., the differential pressure between the inlet and outlet chambers) is proportional to the air flow rate. In the embodiment of FIG. 1, the pressure in the outlet chamber 26 is presumed to be at ambient. It will be appreciated by those of ordinary skill in the art however that the pneumotachometer may be modified in order to provide a second pressure port for sensing the outlet chamber pressure, as is shown in the alternate pneumotachometers of FIGS. 8–11. The transducer 276 (FIG. 12) provides an output signal which is proportional to the difference between the inlet chamber pressure and ambient and thus, which is indicative of air flow rate. Further, the output signal of pressure transducer 276 can be integrated to provide an indication of the patient's breath volume.

Generally, the pneumotachometer 10 is disposable, but the tubing 274 (FIG. 12) coupled between the pneumotachometer and the sensing electronics is reusable. For this reason, it is particularly important to reduce contamination of the tube in order to prevent the spread of disease amongst patients.

Figure 6:
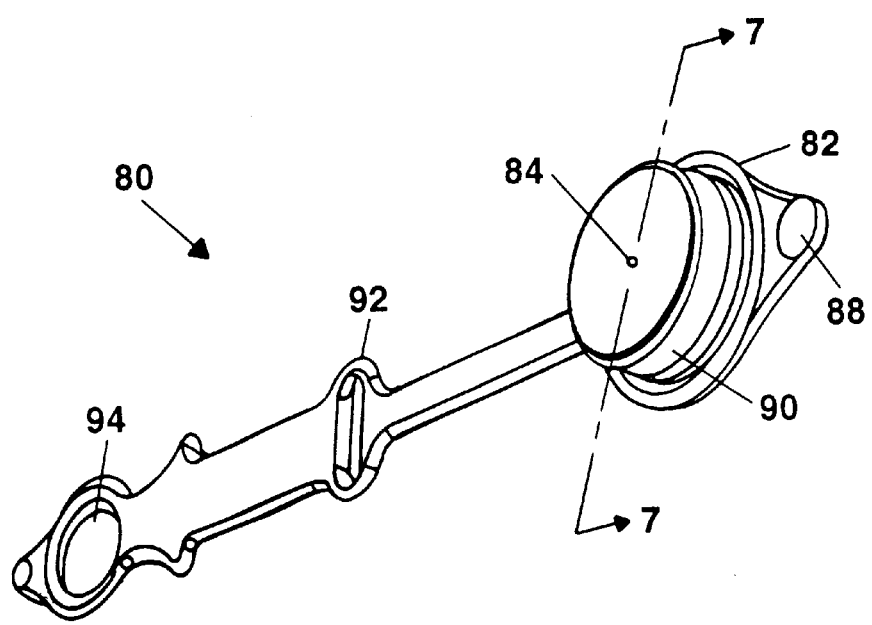
FIG. 6 is an isometric view of a plug adapted for restricting the air flow through the pneumotachometer of FIG. 1.

According to a further aspect of the invention, the resistive element 20 is provided by a bacterial filter material comprising a web of electrostatically charged, hydrophobic (i.e., non-moisture absorbent) fibers. Use of a bacterial filter material, as contrasted to the conventional membrane, enhances the contagion isolation achieved with the present invention, both by its placement between the inlet 14 and the pressure port 30 and between the inlet and the Valsalva plug 80 (FIG. 6).

Various bacterial filter materials are suitable for use as the resistive element 20. One such material is sold under the product name Filtrete™ Air Filter Media, GS-85, by 3M Filtration Products of St. Paul, Minn. However, different performance criteria will dictate the choice of material for different applications. For example, in some applications, a high level of desired contagion protection may dictate that the choice of material be based on its density. In other applications, a limit on acceptable backpressure (i.e., a back resistance to flow) may dictate the choice of material. The maximum backpressure recommended by the American Thoracic Society for a compliant spirometer is 2.8 cm $H_2O$, or 2.060 mm Hg. It will be appreciated by those of ordinary skill in the art that backpressure is related to material density and cross-sectional area. In particular, as the density increases, the backpressure increases; whereas, as the cross-sectional area increases, the backpressure decreases. Thus, for example, backpressure can be maintained constant by increasing both the density and the cross-sectional area. Further, the cross-sectional area of the resistive element may be increased in various ways, such as by simply increasing the pneumotachometer dimensions in the area across which the resistive element is located or by providing pleats in the resistive element. In the illustrative embodiment, the backpressure limit of 2.060 mm Hg is met by using as the resistive element the above-referenced 3M Filtration Products material which has a density on the order of 85 grams/meter$^2$ and providing the resistive element with a cross-sectional area on the order of 1.33 in$^2$.

While use of a bacterial filter material for the resistive element 20 somewhat increases the flow resistance through the pneumotachometer 10, the increased resistance does not noticeably affect the proportional relationship between air flow rate and differential pressure. For example, the pneumotachometer 10 with a resistive element comprising Filtrete™ GS-85 is well suited for use in conjunction with the Valsalva and metronomic deep breathing tests, in which typical air flow rates are on the order of less than 3 liters per second. In fact, the higher air flow resistance advantageously increases the signal to noise ratio for low breath flow rates. The pneumotachometer 10 is also suitable for tests requiring higher air flow rates.

Figure 2:
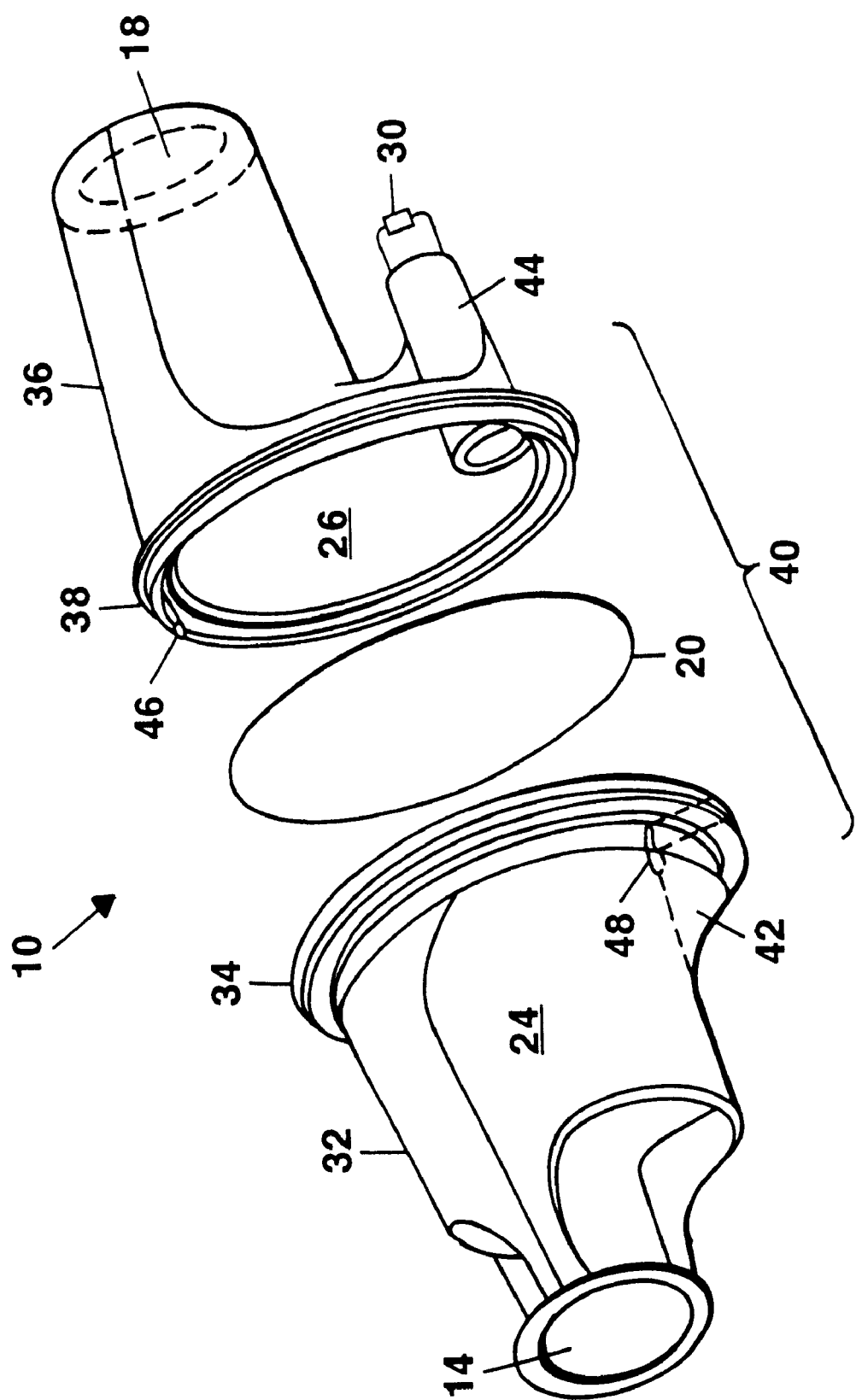
FIG. 2 is an exploded isometric view of the pneumotachometer of FIG. 1.

Referring also to FIG. 2, the pneumotachometer 10 includes a sampling channel 40 through which the static pressure of the inlet chamber 24 is sensed via the pressure port 30 located in the outlet chamber 26. The sampling channel 40 has a first portion 42 disposed in the inlet chamber 24 in gaseous communication with the inlet chamber through at least one aperture 48 and a second portion 44 disposed in the outlet chamber 26 in gaseous communication with the first channel portion 42 and with the pressure port 30, but isolated from the outlet chamber.

The illustrative pneumotachometer 10 is fabricated from two housing portions; an inlet portion 32 and an outlet portion 36. Each of the housing portions 32, 36 has a flange 34, 38, respectively, with features for facilitating assembly, as will be described in conjunction with FIGS. 5A and 5B. In the illustrative embodiment, the two housing portions 32, 36 comprised of High Impact polystyrene and are joined by vibration welding. However, it will be appreciated by those of ordinary skill in the art that other manufacturing techniques may be used, such as adhesives, mechanical clamp rings, threads or snaps.

In assembly, the first sampling channel portion 42 and the second sampling channel portion 44 are axially aligned such that a substantially air tight seal is formed between the two portions. Because the pressure sense tube 274 (coupled between the port 30 and the transducer 276, FIG. 12) is sealed at the transducer, there is virtually no flow across the portion of the resistive element separating the first and second sampling channel portions 42, 44. Thus, there is negligible pressure drop across the portion of the resistive element located between channel portions 42, 44. Thus, the pressure sensed through the pressure port 30 provides an accurate indication of the inlet chamber pressure.

Figure 3:
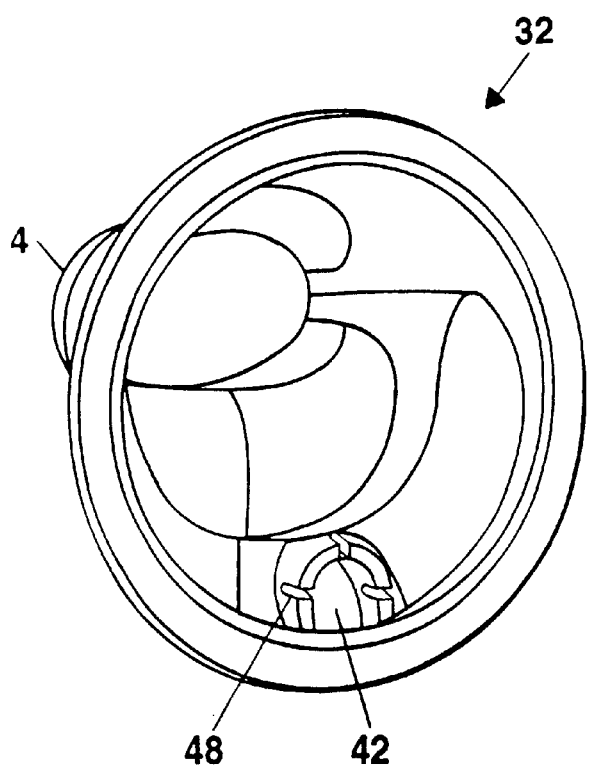
FIG. 3 is an isometric view of the inlet portion of the pneumotachometer of FIG. 1.

Referring also to FIG. 3, the inlet housing portion 32 of the pneumotachometer 10 is shown. The aperture 48 in the first sampling channel portion 42 is provided in the form of a plurality of slots which terminate at the edge of the first channel portion adjacent to the second channel portion 44. This particular arrangement advantageously simplifies the injection molding process used to form the inlet housing portion 32. The size and number of slots providing the aperture 48 may be readily varied, but should be large enough to prevent the aperture from being blocked by saliva or condensation.

Figure 4:
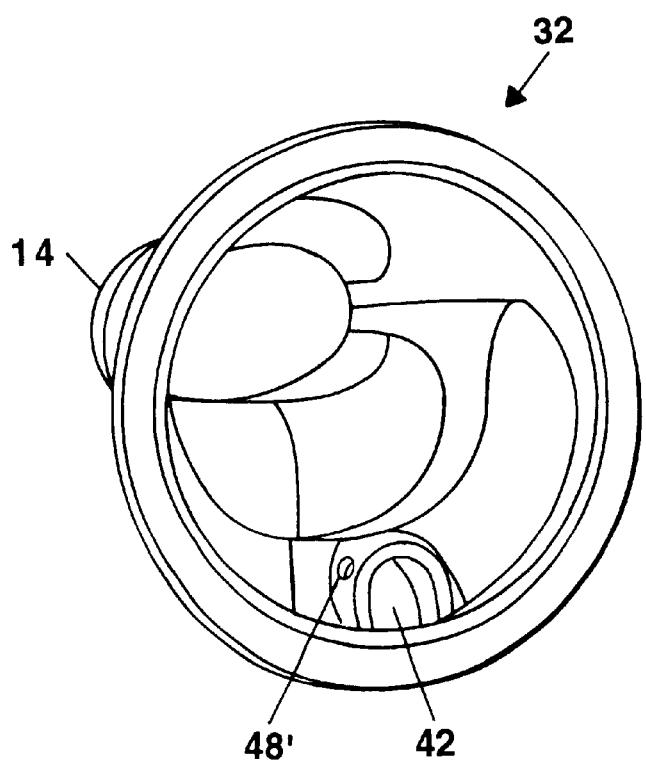
FIG. 4 illustrates an alternate inlet portion for the pneumotachometer of FIG. 1.

It will be appreciated by those of ordinary skill in the art however, that the aperture 48 may be provided in various forms. As one alternative, the aperture may be provided by one or more round holes 48', as shown in the alternative housing portion 32' of FIG. 4.

Figure 5:
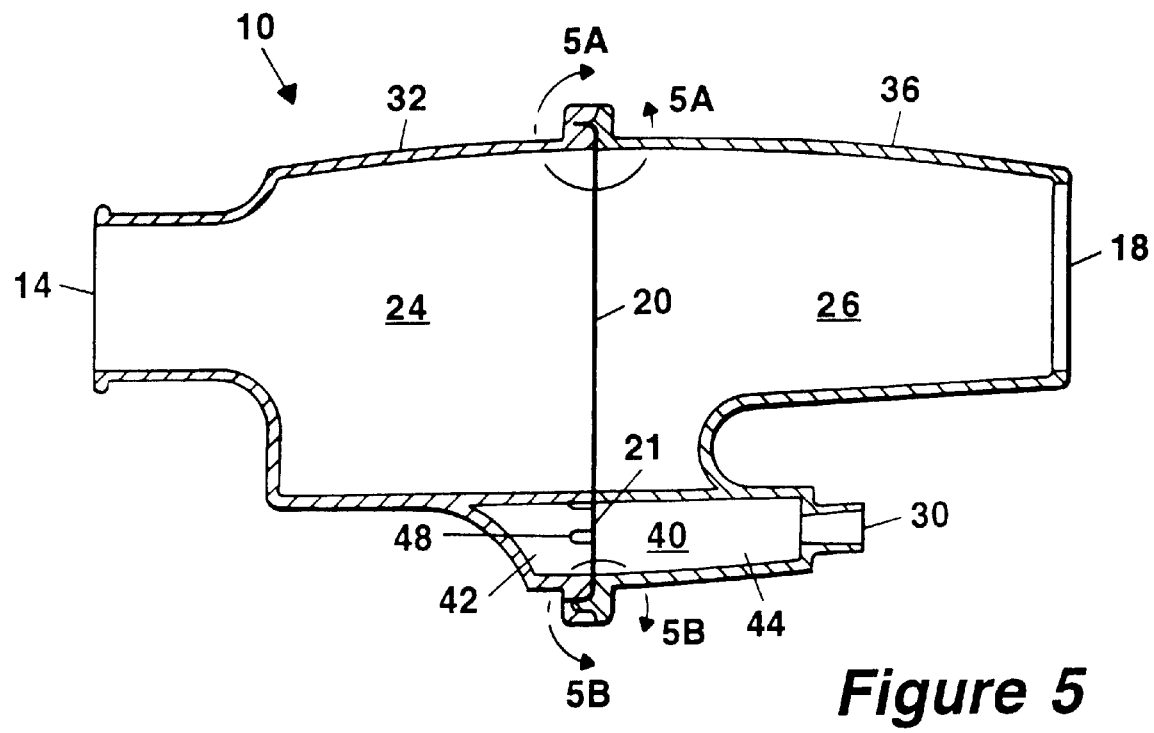
FIG. 5 is a cross-sectional side view of the pneumotachometer of FIG. 1 taken along line 5—5 of FIG. 1.

Referring also to FIG. 5, a cross-sectional side view of the pneumotachometer 10 is shown to include the inlet chamber 24 and the outlet chamber 26, which are formed by joining the inlet housing portion 32 and the outlet housing portion 36 with the resistive element 20 positioned at the junction of the housing portions. Also shown is the sampling channel 40 comprising first channel portion 42 disposed in the inlet chamber 24 in gaseous communication with the inlet chamber through aperture 48 and second channel portion 44 disposed in the outlet chamber 26 in air tight communication with the first portion 42 through a portion 21 of the resistive element 20 and with the pressure port 30.

Figure 5A:
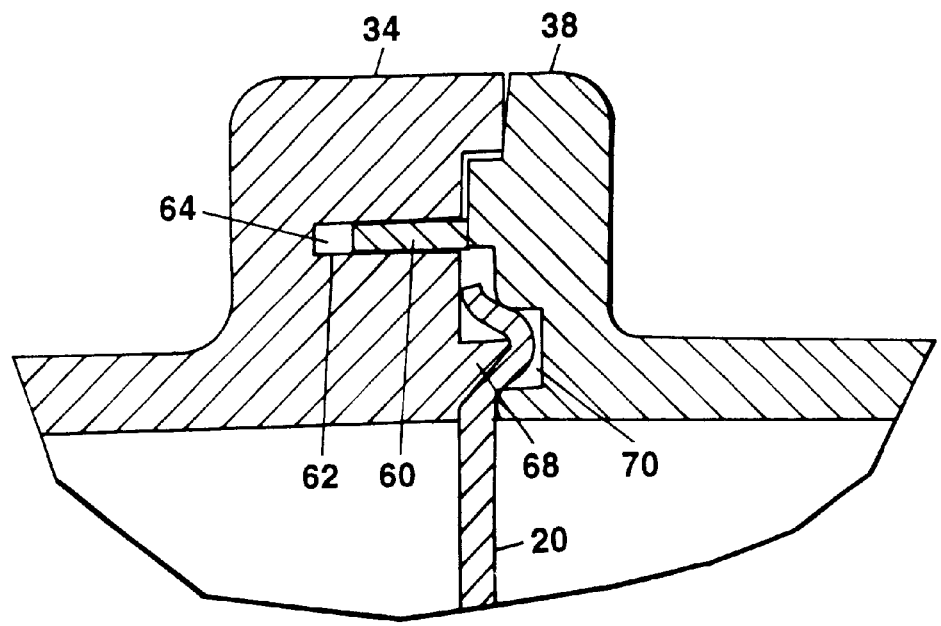
FIG. 5A is an exploded view of a portion of the pneumotachometer taken along line 5A—5A of FIG. 5.
Figure 5B:
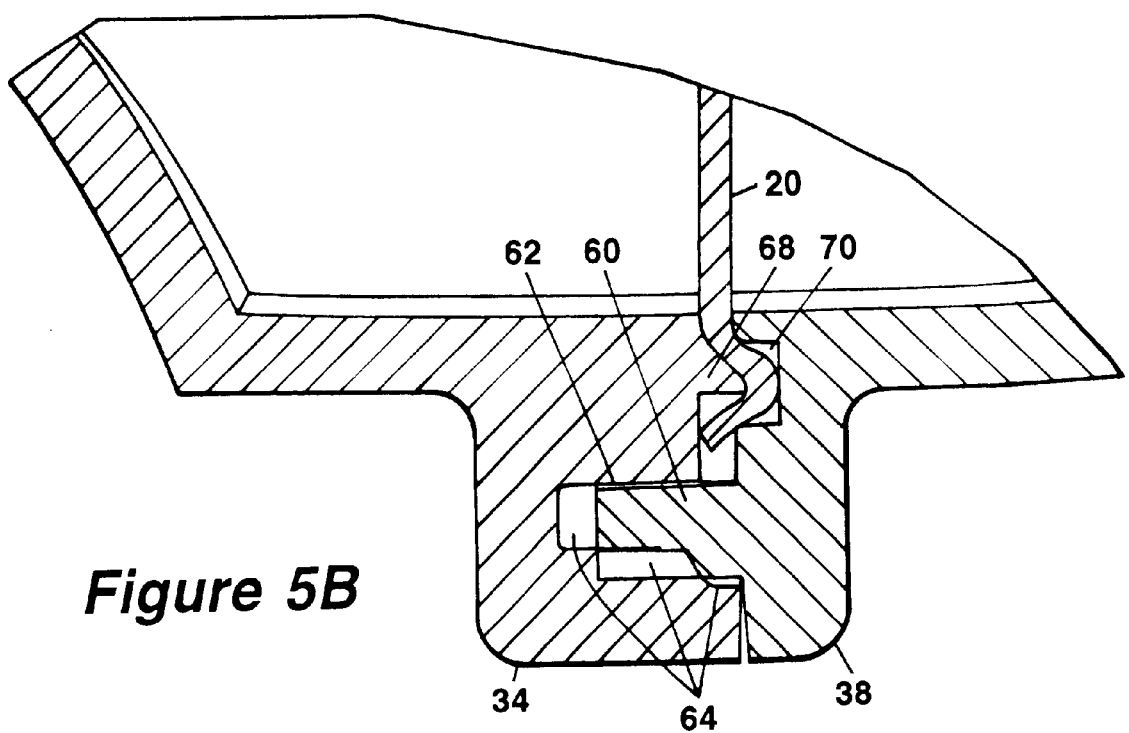
FIG. 5B is an exploded view of a portion of the pneumotachometer taken along line 5B—5B of FIG. 5.

As noted above, the inlet housing portion 32 has a flange 34 adapted to mate with a flange 38 on the outlet housing portion 36. Referring also to FIGS. 5A and 5B, flange 38 has a lip 60 extending around its circumference which is sized and shaped to mate with a complementary groove 62 in the flange 34. More particularly, groove 62 is slightly larger than the lip 60 so that when the two housing portions 32 and 36 are mated, prior to vibration welding, there are hollow areas (labeled 64) which are filled by portions of the flange 38 as a result of the vibration welding process. Thus, it will be appreciated that the cross-sectional views of FIGS. 5A and 5B represent the device after the two housing portions are mated but before the portions are welded together.

Also provided on the flange 34 is a barb 68 which extends around the circumference of the flange and which engages the filter material 20 in assembly in order to hold the filter material securely in place between the two housing portions 32, 36. In assembly, the barb 68 is aligned with a detent 70 in the flange 38. Once the housing portions 32, 36 are brought together with the filter material 20 extending over the barb, the filter material is pushed into the detent 70 and engaged by the barb, as shown.

The flanges 34, 38 are provided with a keying mechanism, such as the detent 46 on flange 38 (FIG. 2) which is adapted to receive a tab on flange 34. The keying mechanism ensures accurate radial alignment of the housing portions 32, 36. It will also be appreciated that the flanges 34, 38 and their features may be modified and yet still achieve secure coupling of the housing portions 32, 36 with the filter 20 extending across the junction of the housing portions.

Referring also to FIG. 6, an isometric view of a Valsalva plug 80 suitable for use with the pneumotachometer 10 is shown. The plug 80 includes an end cap 82 adapted for placement over the outlet 18, an aperture 92 through which the tubing 274 (FIG. 12) extends, and an aperture 94 for hanging the tubes on a hook (not shown). The end cap 82 has a raised portion 90 sized and shaped to be inserted into the outlet 18. The end cap 82 additionally has a relatively small diameter aperture 84 and a tab 88. The tab 88 is used to remove the end cap 82 from the outlet 18 following use. In the illustrative embodiment, the Valsalva plug 80 is comprised of an injection moldable elastomer.

Figure 7:
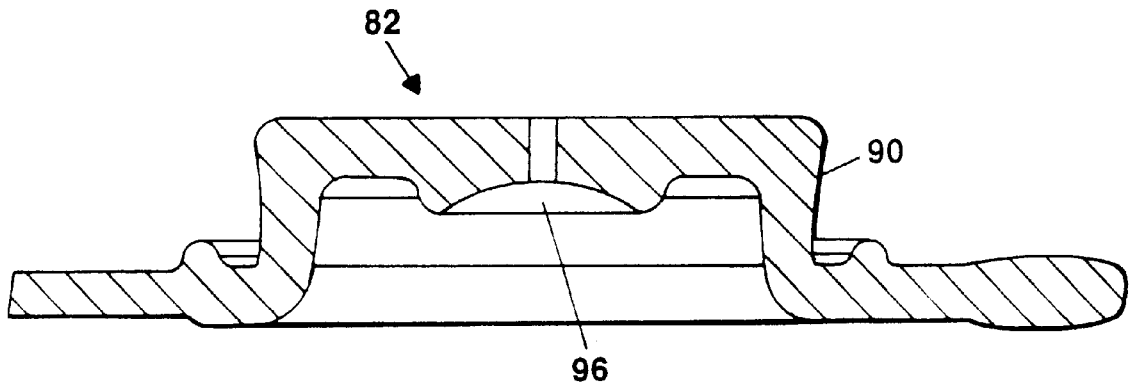
FIG. 7 is a cross-sectional side view of a portion of the plug of FIG. 6 taken along line 7—7 of FIG. 6.

Referring also to the cross-sectional side view of the end cap 82 shown in FIG. 7, a finger detent 96 is provided in order to facilitate placement of the raised portion 90 in the outlet 18. More particularly, pushing on the finger detent 96 causes the end cap 82 to collapse around the finger, thereby permitting the raised portion to be placed easily in the outlet.

With this arrangement, the air flow path through the pneumotachometer 10 is restricted, enabling the patient to achieve a desired expiration pressure, such as 40 mmHg. Aperture 84 is provided in order to prevent the patient from maintaining the desired static pressure by using the air in the mouth only (i.e., the aperture causes a small air leak which requires the patient to continue exhalation in order to maintain the desired expiration pressure) with an open glottis. A suitable size for the aperture 84 is on the order of 1 mm.

Figure 8:
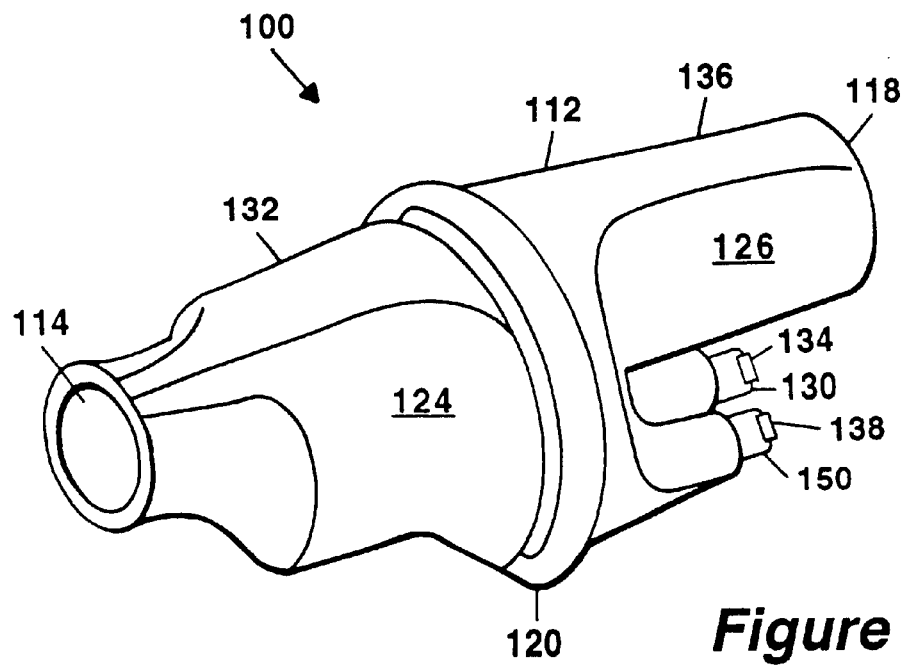
FIG. 8 illustrates an alternate pneumotachometer including a second pressure port for sensing the pressure in the outlet chamber.

Referring also to FIG. 8, an alternate pneumotachometer 100 includes a housing 112 having an inlet 114 through which a patient breathes and an outlet 118 through which air exits or enters the pneumotachometer depending on whether the patient is exhaling or inhaling, respectively. A resistive element 120 divides the housing 112 into an inlet chamber 124 and an outlet chamber 126 and causes a pressure differential to be developed between the chambers. A pressure port 130 for sensing the static pressure in the inlet chamber 124 is located in the outlet chamber, as shown. With this arrangement, the resistive element 120, in addition to creating a pressure differential between the inlet and outlet chambers, serves the purpose of isolating the pressure port 130 from contagions.

The pneumotachometer 100 differs from pneumotachometer 10 (FIGS. 1–3) in that a second pressure port 150 is provided through which the static pressure in the outlet chamber is sensed. In use, the pressure port 130 is adapted for coupling to a first input of a differential pressure transducer 276 (FIG. 12) and the pressure port 150 is adapted for coupling to a second input of the differential pressure transducer through respective tubes 274 for measurement of the pressure gradient across the resistive element 120. For this purpose, pressure ports 130 and 150 are provided with Luer lock fittings 134, 138, respectively, for coupling to a Luer lock of the respective tube. Actual sensing of the static pressure in the outlet chamber 126 with this arrangement may slightly increase the accuracy of the resulting air flow signal since a slight change in pressure from ambient may occur in the outlet chamber due to the velocity of the air flow.

Figure 9:
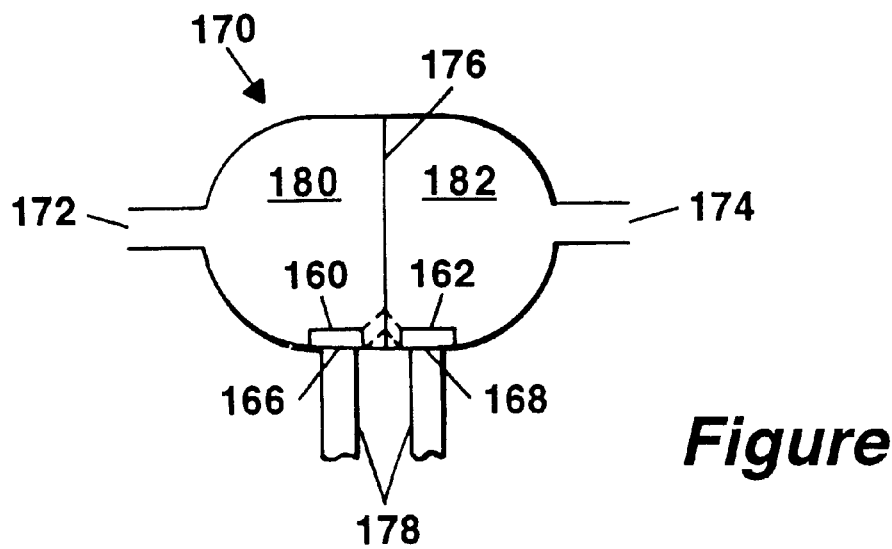
FIG. 9 shows a further alternate pneumotachometer in which the inlet chamber and outlet chamber pressure ports are covered by a bacterial filter material.

Referring to FIG. 9, a simplified cross-sectional view of an alternate pneumotachometer 170 is shown to include an inlet 172, an outlet 174, and a resistive element 176 located between the inlet and outlet and dividing the pneumotachometer into an inlet chamber 180 and an outlet chamber 182. Also provided is a first pressure port 166 located in the inlet chamber 180 through which the inlet chamber pressure is sensed and a second pressure port 168 located in the outlet chamber 182 through which the outlet chamber pressure is sensed. Tubes 178 couple the pressure ports 166, 168 to spirometer electronics.

Filters 160, 162 in the form of a bacterial filter material cover both the inlet chamber pressure port 166 and the outlet chamber pressure port 168, as shown. With this arrangement, the filters 160, 162 provide a barrier to contagions and moisture which might otherwise enter the pressure ports 166, 168 and adversely affect the reusable tubing 178 and electronics coupled to the pressure ports. In the illustrated embodiment, the resistive element 176 comprises a bacterial filter material. The filters 160, 162 may be separate from the resistive element 176 or alternatively, may be extensions of the resistive element 176 (as illustrated by the dotted lines joining the resistive element 176 to the filters 160 162).

It will be appreciated that various modifications to the embodiment of FIG. 9 are possible while still enjoying the benefits of having filters 160, 162 cover pressure ports 166, 168, respectively. As one example, the resistive element 176 may be provided in the form of a conventional membrane, as opposed to a bacterial filter material. This modification is possible while still providing the pneumotachometer with reduced risk of contamination because the filters 160, 162 serve the purpose of reducing contamination. As another alternative, the pneumotachometer 170 may be modified so that only the inlet chamber pressure is sensed through pressure port 160 and the outlet chamber pressure is presumed to be at ambient.

Figure 10:
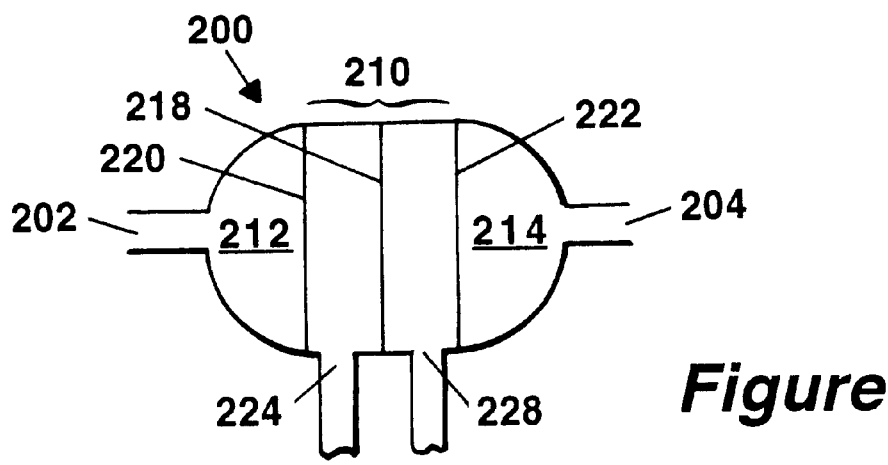
FIG. 10 shows pneumotachometer in which the resistive element includes bacterial filter layers and a membrane.

Referring also to FIG. 10, a further alternate pneumotachometer 200 includes an inlet 202, an outlet 204, and a resistive element 218 located between the inlet and outlet to divide the pneumotachometer into an inlet chamber 212 and an outlet chamber 214. In the embodiment of FIG. 10, the resistive element 218 is provided by a membrane. Also provided are bacterial filters 220 and 222 disposed on either side of the membrane, as shown. A first pressure port 224 through which the inlet chamber pressure is sensed is positioned between filter layer 220 and the membrane 218 and a second pressure port 228 through which the outlet chamber pressure is sensed is positioned between filter layer 222 and the membrane 218. With this arrangement, the bacterial filters 220, 222 isolate the patient's mouth from the pressure ports 224, 228 while the membrane 218 creates the pressure gradient between the inlet chamber 212 and the outlet chamber 214.

Figure 11:
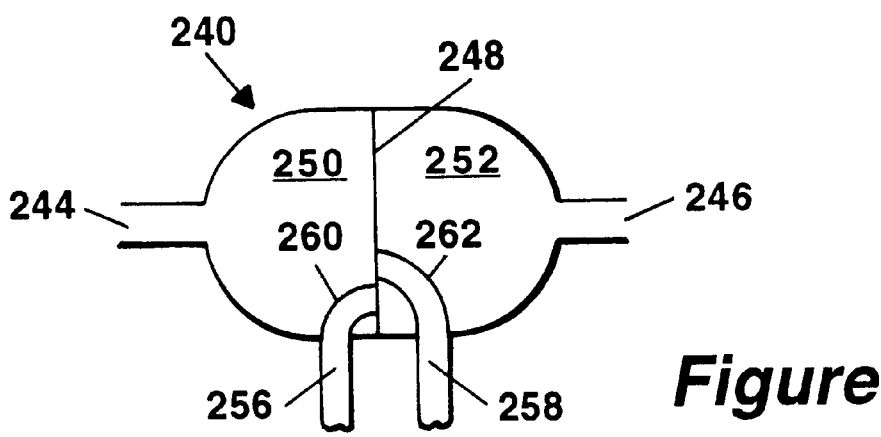
FIG. 11 illustrates a pneumotachometer in which the inlet chamber pressure port is located in the outlet chamber and the outlet chamber pressure port is located in the inlet chamber with both such pressure ports covered by a bacterial filter material.

Referring also to FIG. 11, another pneumotachometer 240 is shown to include an inlet 244, an outlet 246, and a resistive element 248 in the form of a bacterial filter material positioned to divide the pneumotachometer into an inlet chamber 250 and an outlet chamber 252. In this embodiment, a first pressure port 256 is located in the inlet chamber in isolated gaseous communication with the outlet chamber through a tube 260 and a second pressure port 258 is located in the outlet chamber in isolated gaseous communication with the inlet chamber through a tube 262. In use, the pressure in the inlet chamber 250 is sensed through the second pressure port 258 and the pressure in the outlet chamber 252 is sensed through the first pressure port 256. With this arrangement, the bacterial filter 248 isolates the patient's mouth from the first pressure port 258 and both pressure ports are effectively covered by the bacterial filter material of the resistive element. Additionally, any effect on the flow signal caused by the increased resistance of the bacterial filter material is applied equally to both pressure sense ports, thereby canceling any effect on the resulting differential flow signal.

Referring also to FIG. 12, an illustrative medical testing system in the form of a heart rate monitor 270 for use with the inventive pneumotachometer (e.g., pneumotachometer 10 of FIG. 1) is shown. The heart rate monitor 270 includes a processor 280, a user interface 284, a memory 286, a display 290 responsive to a digital I/O board 288. The monitor 270 utilizes various patient interface devices for measuring physiological signals of the patient. For example, the pneumotachometer 10 is adapted for coupling to spirometer electronics 275 via one or more tubes 274 for providing a signal to processor 280 indicative of the patient's breath flow rate. Additional patient interface devices 294, such as ECG electrodes and a blood pressure cuff, and associated processing electronics, may also be provided.

The spirometer electronics 275 includes a pressure transducer 276 and interface electronics 278. In the illustrative embodiment, the pressure transducer 276 includes a first pressure transducer 276a for measuring the pressure at which the patient exhales for use in connection with the Valsalva test and a second pressure transducer 276b for measuring the patient's inspiration and expiration flow for use in connection with the metronomic deep breathing test. More particularly, when the metronomic deep breathing test is performed, pressure transducer 276a is coupled to the pneumotachometer 10 via tube 274 and measures the pressure differential across the resistive element 20 in the pneumotachometer 10 to provide a pressure transducer output signal indicative of the pressure at which the patient breathes, which is proportional to flow rate. When the Valsalva test is performed, pressure transducer 276b is coupled to the pneumotachometer 10 and the outlet 18 is covered by the Valsalva plug 80 (FIGS. 6 and 7). The output signals of the pressure transducer 276 are coupled to interface electronics 278 which may include amplifiers and an analog-to-digital (A/D) converter. It will be appreciated by those of ordinary skill in the art that while two different pressure transducers are used in the illustrated heart rate monitor 270, a single pressure transducer may alternatively be used.

The processor 280 executes programming instructions by which a patient's heart rate variability is analyzed in response to the measured physiological data, such as an ECG signal and optionally, also a blood pressure signal. In the illustrative embodiment, the processor performs R-wave detection processing on the patient's ECG signal of the type described in U.S. Pat. No. 5,984,954, entitled "Methods and Apparatus for R-Wave Detection." Additionally, processor 280 monitors the flow rate signals to ensure proper performance of the desired breathing maneuvers. The breath flow rate signals may additionally be used to provide patient feedback in order to assist the patient in complying with the desired breathing maneuver as is described in U.S. Pat. No. 6,106,481, entitled "Method And Apparatus For Enhancing Patient Compliance During Inspiration Measurements."

The processor 270 may take various forms, such as a conventional microprocessor of a standard personal computer, workstation or other microprocessor-driven device. As one example, the processor 270 is an INTEL-compatible microprocessor of an IBM-compatible personal computer running the MICROSOFT WINDOWS graphical user interface. The memory 286 includes a Random Access Memory (RAM) for temporary data storage and a device with read/write access for permanent data storage, such as a hard drive. The user interface 284 may be provided by a number of conventional devices, such as a keyboard, touch screen, and/or mouse. In one illustrative embodiment, the user interface 284 includes a touch screen incorporated into the display 290 and the display is a flat panel LCD display. It will be appreciated by those of ordinary skill in the art that many of the components described herein may be implemented with various hardware and software.

Having described the preferred embodiments of the invention, it will now become apparent to one of ordinary skill in the art that other embodiments incorporating their concepts may be used.

For example, it will be appreciated by those of ordinary skill in the art that the inlet and/or outlet of the described pneumotachometers can be readily adapted to mate with standard tapered fittings used in medical apparatus, such as ISO standard 5356-1 fittings, for various spirometry and other applications.

Further, it will be appreciated by those of ordinary skill in the art that the various aspects of the present invention (e.g., sensing the inlet chamber pressure through a pressure port located in the outlet chamber, use of a bacterial filter material as the resistive element, and covering at least one pressure port with a bacterial filter material) may be combined into a single pneumotachometer or may be implemented individually.

It is felt therefore that these embodiments should not be limited to disclosed embodiments but rather should be limited only by the spirit and scope of the appended claims. All publications and references cited herein are expressly incorporated herein by reference in their entirety.

What is claimed is:

1. A differential pressure pneumotachometer comprising:
   a housing having an inlet and an outlet;
   a resistive element disposed between said inlet and outlet to divide said housing into an inlet chamber and an outlet chamber and to generate a pressure difference between said inlet chamber and said outlet chamber as air flows between said inlet chamber and said outlet chamber; and
   a pressure port disposed in said outlet chamber in isolated gaseous communication with said inlet chamber, wherein the pressure in said inlet chamber is sensed through said pressure port.

2. The pneumotachometer of claim 1 further comprising a sampling channel extending between said inlet chamber and said outlet chamber, said sampling channel having a first portion disposed in said inlet chamber in gaseous communication with said inlet chamber through at least one aperture and a second portion disposed in said outlet chamber in gaseous communication with said pressure port, wherein a portion of said resistive element is disposed between said first and second channel portions.

3. The pneumotachometer of claim 2 wherein said at least one aperture comprises at least one slot.

4. The pneumotachometer of claim 1 wherein said resistive element comprises a bacterial filter material.

5. The pneumotachometer of claim 1 further comprising a second pressure port through which the pressure in said outlet chamber is sensed.

6. The pneumotachometer of claim 5 wherein said second pressure port is disposed in said outlet chamber.

7. The pneumotachometer of claim 5 wherein said second pressure port is disposed in said inlet chamber.

8. The pneumotachometer of claim 1 wherein said pressure port is covered by a bacterial filter material.

9. A method for sensing respiratory air flow comprising the steps of:
   directing a flow of air through a housing having an inlet, an outlet and a resistive element disposed between said inlet and said outlet to separate said housing into an inlet chamber and an outlet chamber; and
   sampling the pressure in said inlet chamber through a pressure port disposed in said outlet chamber.

10. The method of claim 9 further comprising the step of sampling the pressure in the outlet chamber through a second pressure port disposed in said outlet chamber.

11. The method of claim 9 further comprising the step of providing said housing with a channel having a first portion disposed in the inlet chamber in gaseous communication with the inlet chamber through an aperture and a second portion disposed in the outlet chamber in gaseous communication with said pressure port.

12. The method of claim 9 further comprising the step of providing resistive element in the form of a bacterial filter material.

13. The method of claim 9 further comprising the step of covering said pressure port with a bacterial filter material.

14. A differential pressure pneumotachometer comprising:
   a housing having an inlet and an outlet;
   a resistive element disposed between said inlet and outlet to divide said housing into an inlet chamber and an outlet chamber and to generate a pressure difference between said inlet chamber and said outlet chamber as air flows between said inlet chamber and said outlet chamber; and
   a pressure port through which the pressure in said inlet chamber is sensed; and
   a bacterial filter material disposed over said pressure port.

15. The pneumotachometer of claim 14 wherein said pressure port is disposed in said outlet chamber in isolated gaseous communication with said inlet chamber.

16. The pneumotachometer of claim 14 further comprising a second pressure port through which the pressure in said outlet chamber is sensed and wherein said bacterial filter material is disposed over said second pressure port.

17. The pneumotachometer of claim 16 wherein said second pressure port is disposed in said inlet chamber in isolated gaseous communication with said outlet chamber.

18. A differential pressure pneumotachometer comprising:
   a housing having an inlet and an outlet;
   a bacterial filter material disposed between said inlet and outlet to divide said housing into an inlet chamber and an outlet chamber and to generate a pressure difference between said inlet chamber and said outlet chamber as air flows between said inlet chamber and said outlet chamber; and
   a pressure port through which the pressure in said inlet chamber is sensed, wherein said pressure port is disposed in said outlet chamber in isolated gaseous communication with said inlet chamber.

19. The pneumotachometer of claim 18 further comprising a second pressure port through which the pressure in said outlet chamber is sensed.

20. The pneumotachometer of claim 19 further comprising a bacterial filter material disposed over at least one of said first and second pressure ports.

* * * * *